United States Patent
Lorenzen et al.

(10) Patent No.: US 10,918,035 B2
(45) Date of Patent: Feb. 16, 2021

(54) HIGH PROTEIN PEA CULTIVAR

(71) Applicant: FTE Genetics, LLC, Oskaloosa, IA (US)

(72) Inventors: Jerry Lorenzen, Oskaloosa, IA (US); Kyle Olson, Oskaloosa, IA (US)

(73) Assignee: FTE GENETICS, LLC, Oskaloosa, IA (US)

( * ) Notice: Subject to any disclaimer, the term of this patent is extended or adjusted under 35 U.S.C. 154(b) by 10 days.

(21) Appl. No.: 16/273,038

(22) Filed: Feb. 11, 2019

(65) Prior Publication Data

US 2019/0246588 A1    Aug. 15, 2019

Related U.S. Application Data

(60) Provisional application No. 62/629,336, filed on Sep. 12, 2018.

(51) Int. Cl.
*A01H 6/54* (2018.01)
*A01H 5/10* (2018.01)

(52) U.S. Cl.
CPC .............. *A01H 5/10* (2013.01); *A01H 6/546* (2018.05)

(58) Field of Classification Search
None
See application file for complete search history.

(56) References Cited

U.S. PATENT DOCUMENTS

| | | | |
|---|---|---|---|
| 7,425,668 B2 * | 9/2008 | Warkentin | A01H 5/10 435/430 |
| 7,479,580 B2 | 1/2009 | Warkentin | |

* cited by examiner

*Primary Examiner* — Matthew R Keogh
(74) *Attorney, Agent, or Firm* — Marguerite L. Yang; Jeanette M. Braun; Peter K. Trzyna

(57) ABSTRACT

A new field pea cultivar designated PP-1804-4, seeds of field pea cultivar PP-1804-4, plants of field pea cultivar PP-1804-4, plant parts of field pea cultivar PP-1804-4, and methods for producing a field pea plant produced by crossing field pea cultivar PP-1804-4 with itself or with another field pea cultivar, and the creation of variants by mutagenesis or transformation of field pea cultivar PP-1804-4 are disclosed. Commercial commodity products from the seeds of field pea cultivar PP-1804-4, food products comprising these commercial commodity products, and methods for making the same are also disclosed.

20 Claims, No Drawings

HIGH PROTEIN PEA CULTIVAR

CROSS-REFERENCE TO RELATED APPLICATIONS

The application claims the benefit of U.S. Provisional Patent Application No. 62/629,336, filed Feb. 12, 2018, entitled "High Protein Pea Cultivar", which is hereby incorporated by reference in its entirety as if fully restated herein.

BACKGROUND

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single cultivar an improved combination of desirable traits from the parental germplasm. In the case of this inventive field pea cultivar the important traits include, but are not limited to, increased disease resistance, increased ease of harvesting, increased resistance to shattering, increased drought resistance, and increased pea seed protein content.

Field pea (*Pisum sativum* L.), an annual legume, is also commonly referred to as field pea and dry pea. Field pea most likely originated in Southwest Asia and is widely grown in Russia, China, Canada, Europe, Australia and the United States. Traditionally it was primarily used as a grain crop, for livestock feed or as a vegetable. Field pea is among the oldest crops in the world as it was cultivated as early as 9000 years ago. Field pea is a grain legume commonly used throughout the world in human cereal grain diets. A growing commercial use of field peas is as a source of protein, as well as a source of starch and dietary fiber. This use as a source of protein is especially important as consumers become more aware of their protein consumption and become more cautious in consuming protein from allergenic sources, such as meat, eggs, milk, and soybeans. As field peas are a growing source of protein, the protein content of field peas is important. The higher the protein content, the more marketable the harvested peas.

Current commercial field peas comprise about 18-20% protein (on a dry basis). The protein in field peas is rich in the amino acids lysine and tryptophan as compared to cereal grains. Field peas also contain high levels of carbohydrates and fiber (especially fiber in the pea hull) and contain a large percentage of total digestible nutrients, which makes them excellent human and livestock feed. Also, field peas contain 5 to 20% less of the trypsin inhibitors than soybean. This allows it to be directly fed to livestock without having to go through an extrusion heating process.

There are two main types of field peas. One type comprises smooth seeds (i.e., peas) and is used primarily for food and feed. The other type comprises wrinkled seeds and is usually harvested when immature and used for freezing and canning. Peas may comprise either green or yellow cotyledons under a white or sometimes pale green seed coat. Field pea seeds weigh from 100 to 350 g/1000 seeds when dry and mature.

Most pea varieties produce white to reddish-purple flowers, which are self-pollinated. Each flower will produce a pod containing four to nine seeds. Pea varieties are traditionally of either indeterminate or determinate flowering habit and normally flower 40-50 days after planting. Determinate flowering varieties will flower for long periods and ripening can be prolonged under cool, wet conditions. Indeterminate varieties are later in maturity ranging from 90 to 100 days. Determinate varieties will flower for a set period and ripen with earlier maturity of 80 to 90 days. As listed in Table 1, the field pea cultivar of this invention comprises white flowers, a medium time of flowering (50-60 days after planting), and are between indeterminate and determinate, with an early to moderated maturity duration (about 90 days).

Field pea plants can be grown in colder climates of North Dakota, Canada, and Minnesota. Dry hot climates can affect plant germination, flowering, and plant maturity. Field peas are sensitive to heat stress at flowering. In both drier and sandier soil environments, current commercially available pea cultivar pea plants have difficulty getting enough water to grow and flower. This can reduce pod and pea set. A challenge of harvesting currently commercially available field peas is the tendency of pea pods to dry after maturing and open, dropping the peas to the ground either before or during the rigors of harvesting. This is called shattering. Retrievable yields would increase if field pea plants were bred so that the seal closing the pea pod did not open as the pea pods dried in hot and/or dry climates. Even if the weather was not hot and/or dry, the shattering resistance (i.e., resistance to pea pods opening) would also allow the pea harvesting to be done over a longer period of time after plant maturity—a commercial benefit.

The shatter resistance test comprised planting a 200 seed (i.e., pea) test plot with peas from many varieties. The plants sit in the field for a month after they are ready to harvest (e.g., the plants are brown), during which the plants go through two rain and dry cycles. The plants and their resulting peas are evaluated as to shattering. Usually, a known commercial field pea cultivar, such as Treasure (owned and licensed by Canadian Development Center), is included as a comparison standard. The field is then evaluated as to the amount of seed on the ground due to "shattered" pods.

Field pea plants are harvested using threshers with blades/teeth that slide between pea plants, and between the ground and the area of the pea plant stem where the pea pods are attached. The more vertical the plant growth and the more vertical the plant stems remain after maturity and drying, then more of the peas will be retrieved during harvesting. Remaining vertical is important as field pea plants do not cling to their neighbor plants like soybean plants do. Harvest Ease (rating of 0-9) is a measure of plant's ease to harvest, especially as related to the plants tendency to remain vertical at the time of harvest, The Harvest Ease test was designed and is run by NDSU Carrington, N. Dak. Research Trial. Score of 0=All plants upright, very easy to harvest. Score of 9=All plants flat, very difficult to harvest. Usually a commercially available pea cultivar is included as a standard in each test run. For example Spider, a commercial field pea cultivar, had a Harvest Ease of 0.7. Spider is a field pea variety developed by a plant breeder in the US using genetics from Europe. The breeder is Riverside Communications, Inc. (Montana, US) d/b/a Northern Superior Seed (North Dakota, US). Another commercially available field pea cultivar called Treasure had a Harvest Ease of 2.5. Treasure is a variety owned and licensed by Canadian Development Center (CDC).

Another challenge of efficient commercial field pea growth and harvesting is the many diseases that can affect field pea plants. Wet and cold field conditions (common in Kansas, Iowa, Minnesota, and North Dakota) support many diseases that can damage pea plant growth and harvest. Such diseases include but are not limited to Powdery Mildew, *Mycosphaerella* Blight (*Mycosphaerella pinodes*), Azchoch Root Rot (*Phoma medicagins* var. *pinodella*) and Root Rot (*Fusarium oxysporum* f. Sp plsl).

Below are further discussions of these diseases and how they are rated:

Field Pea Powdery Mildew Rating:

Results are scored as Resistant, Moderately Resistant, Moderately Susceptible and Susceptible.

| | | |
|---|---|---|
| 1. | Resistant | White powdery fungus is not observed or only observed as a small cluster on 1% of lower leaf tissue. Harvested seed has not been affected |
| 2. | Moderately Resistant | White powdery fungus is observed in small clusters on 50% of leaf tissue. Harvested seed does not show any signs of discoloration. Yields are not affected by anyway. |
| 3. | Moderately Susceptible | White Powdery fungus is observed in larger clusters on 50%-75% of leaf tissue. Slight infection of pods is observed. Harvested seeds show a slight discoloration. |
| 3. | Susceptible | White Powdery fungus with grey discoloration is observed on more than 75% of plant tissue including leaves, stems and pods. Harvested seed has a high level of gray-brown discoloration. Overall yields can be reduced 50%-75% |

Powdery mildew can be a very important disease when conditions are favorable. It reduces seed size and can sharply reduce yields if it develops during early to mid-pod development. Late planted peas are at greater risk for yield loss than early planted peas. Field peas susceptible to powdery mildew develop a white powdery fungal growth that covers leaves, stems and pods of infected plants. Fungal growth is favored by dry, warm weather that is accompanied by cool nights when dew develops. Powdery mildew in field peas is caused by the fungus *Erysiphe polygoni*. The disease begins development as small white clusters on lower plant leaves. Once the mildew is observed it can spread very rapidly and cover the entire plant. Severity of the mildew present and plant health can vary due to the amount of resistance or susceptibility. Resources: "Field Pea Disease Review: Powdery Mildew" NDSU (ag.ndsu.edu/cpriplant-pathology/field-pea-diseases-review-powdery-mildew-06-02-16)

Field Pea *Mycosphaerella* Blight Rating:

Results are based on a rating of Resistant, Moderately Resistant, Moderately Susceptible and Susceptible.

| | |
|---|---|
| 1. Resistant | 0-1% of lower leaves show signs of purplish black lesions associated with *Mycosphaerella* Blight. |
| 2. Moderately Resistant | Any purplish black lesions observed on lower leaf tissue progresses covering up to 50% of lower leaves and begins to affect pods and stems. Seed quality is slightly reduced. Plant reaches normal maturity & typical yields. |
| 3. Moderately Susceptible | Purplish black lesions are observed on 50%-75% of plant tissue; leaves, stems and pods. Seed quality and yield are reduced by 50%. |
| 4. Susceptible | Purplish black lesions and brown specs cover 75% or more of plant material; leaves, stems and pods. In most cases stem lesions will weaken the stem and cause lodging. Early maturation can also be observed in susceptible selections. Yields and seed quality are reduced by 75% or more. |

*Mycosphaerella* Blight is caused by the fungus *Mycosphaerella pinodes* and *Ascochyta pinodella* and is most prevalent during periods of cool, wet weather occurring during bloom and early to mid-pod development. This blight forms at the bottom of the pea plant beginning as purplish black specks or lesions with a distinct concentric ring. As the disease progresses the lesions become one mass on the lower leaves and continue to spread through the stem to the pods. As the stem weakens lodging or early maturation will occur. "Identification of *Mycosphaerella* Blight on Field Peas" (ag.ndsu.edu/CarringtonREC/documents/plantpathologyrd/noyeardocs/FIELDPEAMycosphidentfication.pdf)

Root Rot (*Fusarium oxysporum* f, Sp *pisi*) Azchoch Root Rot:

| | |
|---|---|
| 1. Resistant | Seedlings have good emergence. Plants show no signs of stunted growth or yellowing compared to susceptible varieties. |

-continued

| | |
|---|---|
| 2. Moderately Resistant | Seedlings have good emergence. Plant growth is stunted by 25%, yellow of plant tissue is 25%, and root nodules are slightly reduced. |
| 3. Moderately Susceptible | Seedling has slow emergence, growth is stunted by 50% or more, yellow of plant tissue is 50% or more. Roots are slightly underdeveloped, and nodules are reduced by 50% or more. |
| 4. Susceptible | Varieties show poor or no emergence, growth is stunted 75% or more, Yellowing of plant tissue is 75% or more, roots are severely underdeveloped, nodules are very few if any. Death may also occur |

Root Rot is favorable during cool moist weather where soils are water logged. Susceptible varieties can have poor emergence, stunted plant growth, yellowing of plant tissue, poor root development, reduced nodulation and death. Root Rots are initiated by different funguses. Plant tissue analysis is used to identify the strain.

A potential commercial application of a pea cultivar would be rounder, more uniformly shaped peas. Consumers may prefer rounder and more uniformly shaped peas for their appearance. Manufacturers may prefer rounder and more uniformly shaped peas for their ease in processing (e.g., conditioning and packaging). The more round and uniform in shape the peas, the more efficient processing because the peas are now more easily separated from dirt lumps, rocks, and other debris, and whole peas can be separated from split or broken peas. This efficiency can lead to lower processing costs and so lower pea cost to consumer.

Therefore there is a need for a pea cultivar with the increased protein content, uniform spherical shape, increased heat resistance, and increased disease resistance. The breeders (i.e., inventors) of the pea cultivar of the current invention have developed a pea cultivar with these attributes and benefits.

SUMMARY

The disclosure below uses different embodiments to teach the broader principles with respect to articles of manufacture, apparatuses, and processes for using the articles and apparatuses, processes for making the articles and apparatuses, and products produced by the process of making, along with necessary intermediates. This Summary is provided to introduce the idea herein that a selection of concepts is presented in a simplified form as further described below. This Summary is not intended to identify key features or essential features of subject matter, nor is this Summary intended to be used to limit the scope of claimed subject matter. Additional aspects, features, and/or advantages of examples will be indicated in part in the description which follows and, in part, will be apparent from the description, or may be learned by practice of the disclosure.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

With the foregoing in mind, consider a new and distinctive field pea cultivar, *Pisum sativum* (L) designated PP-1804; its seeds, plants, as well as the methods for producing the new field pea cultivar, the commercial commodity products from the seeds, and the food products comprising these commodity products.

Accordingly, there is provided a new field pea cultivar designated PP-1804. The embodiments relate to the seeds of field pea cultivar PP-1804, to the plants of field pea cultivar PP-1804, to plant parts of field pea cultivar PP-1804, and to methods for producing a field pea plant produced by crossing field pea cultivar PP-1804 with itself or with another field pea cultivar, and the creation of variants by mutagenesis or transformation of field pea cultivar PP-1804. The embodiments also relate to the commercial commodity products from the seeds of field pea cultivar PP-1804, and the food products comprising these commercial commodity products.

Thus, any breeding methods using the field pea cultivar PP-1804 are part of these embodiments: selfing, backcrosses, hybrid production, crosses to populations, and the like. All plants produced using field pea cultivar PP-1804 as at least one parent or grandparent are within the scope of this invention. This field pea cultivar could be used in crosses with other, different, field pea plants to produce first generation ($F_1$) field pea hybrid peas and plants with superior characteristics. The instant pea cultivar include, but are not limited to, high pea protein content, increased heat resistance, increased disease resistance, and uniform pea shape.

DETAILED DESCRIPTION MODES
DEFINITIONS

In the description and tables which follow, a number of terms are used. In order to provide a clear and consistent understanding of the specification and claims, including the scope to be given such terms, the following definitions are provided:

Allele: Allele is any or one of more alternative forms of a gene, all of which relate to one trait or characteristic. In a diploid cell or organism, the two alleles of a given gene occupy corresponding loci on a pair of homologous chromosomes.

Backcrossing: Backcrossing is a process in which a breeder repeatedly crosses hybrid progeny back to one of the parents, for example, a first generation hybrid $F_1$ with one of the parental genotypes of the $F_1$ hybrid.

Cotyledon: A cotyledon is a type of seed leaf. The cotyledon contains the food storage tissues of the seed, Disease Resistance: Disease resistance genes comprise the ability to detect a pathogen attack and facilitate a counter attack again the pathogen Embryo. The embryo is the small plant contained within a mature seed.

Emergence: Emergence is the score that indicates the ability of the seed to emerge when planted 3" deep in sand and with a controlled temperature of 25 C. The number of plants that emerge each day are counted. Based on this data, each genotype is given a 1 to 9 score based on its rate of emergence and percent of emergence. A score of 9 indicates an excellent rate and percent of emergence, and intermediate score of 5 indicates average ratings and a 1 score indicates a very poor rate and percentage of emergence.

Harvest Ease: Harvest ease is a score of 0 to 9 given by NDSU Carrington, N. Dak. Research Trials. 0=All plants upright, very easy to harvest. 9=All plants flat, very difficult to harvest.

Hilum: Hilum refers to the scar left on the seed which marks the place where the seed was attached to the pod prior to the seed being harvested.

Hypocotyl: A hypocotyl is the portion of an embryo or seedling between the cotyledons and the root. Therefore, it can be considered a transition zone between shoot and root.

Plant height: Plant height is taken from the top of the soil to the top node of the plant and is measured in centimeters.

Pod: Pod refers to the fruit of a field pea plant. It consists of the hull or shell (pericarp) and the field pea seeds.

Protein Percent: Field pea seeds contain a considerable amount of protein. Protein is generally measured by NIR spectrophotometry, and is reported on an as is percentage basis.

Quantitative Trait Loci (QTL): QTL refer to genetic loci that control to some degree numerically representable traits that are usually continuously distributed.

Regeneration: Regeneration refers to the development of a plant from tissue culture.

Relative Maturity: "Early maturity" is defined as being around 80 days, "medium maturity" is defined as 90-92 days, and "late maturity" is defined as being 98 days and beyond.

Shattering Resistance: Shatter resistance is the tendency of pea pods to remain closed (i.e., sealed) and intact during and after maturity. The seal that keeps the pea pod closed is intact and strong.

Seed Protein Peroxidase Activity: Seed protein peroxidase activity refers to a chemical taxonomic technique to separate cultivars based on the presence or absence of the peroxidase enzyme in the seed coat. There are two types of field pea cultivars: Those comprising high peroxidase activity (dark red color) and those comprising low peroxidase activity (no color).

Seeds Per Pound: Field pea sees vary in seed size, therefore, the number of seeds required to make up one pound also varies. This affects the pounds of seed required to plant a given area and can also impact end uses. Usually peas are measured as weight per 1000 seeds.

Single Gene Converted (Conversion): Single gene converted (conversion) plant refers to plants which are developed by a plant breeding technique called backcrossing wherein essentially all of the desired morphological and physiological characteristic of a cultivar are removed in addition to the single gene transferred into the cultivar via the backcrossing technique or via genetic engineering.

Stem Vine Length: Stem vine length is measure in centimeters from the stem of the plant to the ground and is observed after flowering when pods are fully swollen.

Time of Flowering: Time of flowering is observed when approximately 30% of plants comprise one flower open.

Field pea cultivar PP-1804 of the current disclosure is a yellow field pea with an early—medium relative maturity under Kansas, Iowa, Minnesota, and North Dakota local conditions, which are the currently most common environments for growing commercially available pea cultivars. Field pea cultivar PP-1804 has also been grown successfully in Oklahoma local conditions (which are relatively hotter and dryer than conditions in Kansas, Iowa, Minnesota, and North Dakota).

The field pea cultivar (PP-1804) has shown uniformity and stability, with the plant and seed characteristics described in Table 1, Table 2 and in the following cultivar information in this disclosure. This cultivar has been self-pollinated a sufficient number of generations with careful attention to uniformity of plant type. The cultivar has been increased with continued observations for uniformity.

Table 1 contains the morphological and other characteristics of field pea cultivar PP-1804 based primarily on data collected in Minnesota in 2017. For comparison purposes, Table 1 also contains the morphological and other characteristics for 2 other field pea cultivars: CDC 0001 and CDC 0007, CDC 0001 and CDC 0007 are commercially available pea cultivars supplied by World Food Processing, LLC (Oskaloosa, Iowa). CDC 0001 is disclosed and claimed in U.S. Pat. No. 7,479,580. CDC 0007 is disclosed and claimed in U.S. Pat. No. 7,425,668. PP-1804 is the progeny of CDC 0001 and field pea CRP 0132 (a Single Plant Purification from CDC 0001).

Table 2 contains the morphological and other characteristics of field pea cultivar PP-1804 based primarily on data collected in Minnesota in 2018. For comparison purposes, Table 2 also contains the morphological and other characteristics for 2 other field pea cultivars: PP-0555 and PP-0667. PP-0555 and PP-0667 are commercially available pea cultivars supplied by World Food Processing, LLC (Oskaloosa, Iowa). PP-0555 and PP-0667 comprise one parent (CDC 0001) in common with PP-1804.

TABLE 1

| Cultivar Description Facts (Season 2017 Data) | | | |
|---|---|---|---|
| Table 1: | PP 1804-4 | CDC 0001 | CDC 0007 |
| Plant type: | Yellow field pea | Yellow field pea | Yellow field pea |
| Plant habit: | Between Determinate & Indeterminate | Between Determinate & Indeterminate | Between Determinate & Indeterminate |
| Plant height: | Greater than 50 cm | Greater than 50 cm | Greater than 50 cm |
| Stem vine length: | 70 cm | 90-115 cm | 80 cm |
| Stem fasciation: | Absent | Absent | Absent |
| Presence of leaflets: | Semi leafless | Leafed | Leafed |
| Relative maturity: | Early-medium maturity | Medium | Medium |
| Flower color: | White | White | White |
| Flower color wing: | White | White | White |
| Flower shape at base: | Level or straight | Level or straight | Level or straight |
| Time of flowering: | Medium | Medium | Medium |
| Protein content: | 26% | 25% | 24% |
| Stipule: | | | |
| a) Development: | Normal | Normal | Normal |
| b) Marbling (before flowering): | Present | Present | Present |

TABLE 1-continued

Cultivar Description Facts (Season 2017 Data)

| Table 1: | PP 1804-4 | CDC 0001 | CDC 0007 |
|---|---|---|---|
| c) Maximum density of marbling: | Sparse | Sparse | Between Sparse and Medium |
| Pod length (observed at first flowering node): | Medium | Medium | Medium |
| Medium Width (observed at first flowering node): | Medium | Medium | Medium |
| Curvature (fully swollen): | Absent | Absent | Absent |
| Color (immature): | Light green | Light green | Light green |
| Color (fully swollen): | Green | Green | Green |
| Parchment (dry and papery): | | | |
| a) Shape: | Spherical | Spherical | Spherical |
| b) Size: | Medium | Medium | Medium |
| c) Weight (g/1000 seeds): | 232 | 230 | 230 |
| d) Color of cotyledon: | Yellow field pea | Yellow field pea | Yellow field pea |
| e) Black of hilum: | Absent | Absent | Absent |
| Reaction to Disease: | | | |
| a) Root Rot (*Fusarium oxysporum* f, Sp pisi): | Resistant | Moderately Susceptible | Moderately Susceptible |
| b) *Mycosphaerella* Blight (*Mycosphaerella Pinodes*): | Resistant | Moderately Susceptible | Moderately Susceptible |
| c) Azchoch Root Rot (*Phoma Medicagins* var. *pinodella*): | Resistant | Moderately Susceptible | Moderately Susceptible |
| d) Powdery Mildew: | Resistant | Moderately Susceptible | Moderately Susceptible |
| Shattering | Resistant | | |
| Harvest Ease | 0 | | |

TABLE 2

Cultivar Description Facts: (Season 2018)

| Table 2 | PP-1804 | PP-0667 | PP-0555 |
|---|---|---|---|
| Plant Type | Yellow Field Pea | Yellow Field Pea | Yellow Field Pea |
| Plant Habit | Between Determinate & Indeterminate | Between Determinate & Indeterminate | Between Determinate & Indeterminate |
| Plant Height | Great than 50 cm | Great than 50 cm | Great than 50 cm |
| Stem vine length | 70 cm | 76 cm | 71 cm |
| Stem Fasciation | Absent | Absent | Absent |
| Presence of Leaflets | Semi leafless | Semi leafless | Semi leafless |
| Relative Maturity | Early Medium Maturity | Early Medium Maturity | Early Medium Maturity |
| Flower Color | White | White | White |
| Flower Color Wing | White | White | White |
| Flower Shape at base | Level or Straight | Level or Straight | Level or Straight |
| Time of Flowering | Medium | Medium | Medium |
| Protein Content | 29% | 27% | 28% |

TABLE 2-continued

Cultivar Description Facts: (Season 2018)

| Table 2 | PP-1804 | PP-0667 | PP-0555 |
|---|---|---|---|
| Yield | 47 bu/acre | 45 bu/acre | 46 bu/acre |
| Stipule: | | | |
| a) Development | Normal | Normal | Normal |
| b) Marbling (before Flowering) | Present | Present | Present |
| c) Maximum density of marbling | Sparse | Sparse | Sparse |
| Pod Length (observed at first flowering node) | Medium | Medium | Medium |
| Pod Width (observed at first flowering node) | Medium | Medium | Medium |
| Pod Curvature (fully swollen) | Absent | Absent | Absent |
| Pod Color (Immature) | Light Green | Light Green | Light Green |
| Pod Color (Fully swollen) | Green | Green | Green |
| Parchment (dry & Papery) | Present | Present | Present |
| Seed: | | | |
| a) Shape | Round | Slightly Round | Slightly Round |
| b) Size | Medium | Medium | Medium |
| c) Weight (g/1000 seeds) | 232 | 230 | 231 |
| d) Color of Cotyledon | Yellow | Yellow | Yellow |
| e) Black of Hilum | Absent | Absent | Absent |
| f) Time of Maturity | 79 days | 78 days | 78 days |
| Reaction to Disease | | | |
| a) Root Rot (*Fusarium oxysporum* f, Sp sisi) | Moderately Resistant | Moderately Susceptible | Moderately Susceptible |
| b) Azochoch Root Rot (*Phoma Medicagins* var. *pinodella*) | Moderately Resistant | Moderately Susceptible | Moderately Susceptible |
| c) *Mycospharella* Blight (*Mycospharella Pinodes*) | Moderately Resistant | Moderately Susceptible | Moderately Susceptible |
| d) Powdery Mildew | Resistant | Resistant | Susceptible |
| Shattering | Resistant | Moderately Resistant | Moderately Resistant |
| Harvest Ease | 0 | 0.3 | 0.3 |

As illustrated in Table 1 and Table 2, PP-18094-4 has not only higher protein content, but also more disease resistance than its parent (CDC 0001) as well as more than CDC 0007. Also, though they comprise one parent in common, PP-1804 comprises a combination of characteristics that PP-0555 and PP-0667 do not comprise (for example, both high protein content and greater disease resistance). As already discussed, there would be commercial benefits if a pea cultivar has high pea protein content, increased heat resistance, increased disease resistance, and uniform pea shape. Field pea cultivar PP-1804 does comprise these benefits. As to protein content: currently commercially available field pea cultivars comprise a protein content of 16-20%, whereas the field pea cultivar of the instant disclosure (PP 1804) has a protein content of about 22% to about 30% (on dry basis). Data on the protein content of peas grown from PP-1804 plants in Minnesota (2017 and 2018 growing seasons) and in Oklahoma (2018 growing season) [average of four trials]

had protein content of about 26% (dry content) for Minnesota 2017, about 29% (dry content) for Minnesota 2018, and about 30% for Oklahoma 2018. This data also shows that the pea cultivar of this disclosure (i.e., PP-1804) was successfully grown in the wet and cooler growing conditions of Minnesota (traditional field pea growing conditions) and dryer and hotter growing conditions of Oklahoma. These results show the increased heat stress tolerance of PP-1804, due to the cultivar's reduced shattering and deeper root system than current commercially available cultivars. The field pea plants of this disclosure are additionally bred to be more resistant to drought, and/or sandy soil. In both drier and sandier soil environments, current commercially available pea cultivar pea plants have difficulty getting enough water to grow and flower. The pea plants of this disclosure comprise deeper, larger root systems which allow them to go deeper and farther spread out than traditional pea plants, allowing them to pull water from a larger soil area. Also, field peas are traditionally sensitive to heat stress at flowering, which can reduce pod and pea set. This is not so with the field pea cultivar of this disclosure.

As already discussed, shatter resistance is a commercial benefit. The pea cultivar of this disclosure (PP-1804) was planted along with other pea varieties, including commercially available pea cultivar Treasure, in a shatter resistance test plot. All of the plants sat in the field for a month after they were ready to harvest, during which the plants went through two rain and dry cycles. The results were that PP-1804 pods were all intact, whereas other varieties failed and pods/peas were on the ground. As already discussed, Harvest Ease evaluations rank the ease with which pea plants can be successfully harvested. The pea cultivar of this disclosure (PP-1804), commercially available pea cultivar Spider, commercially available pea cultivar Treasure, and other cultivars were grown and evaluated in NDSU Carrington, N. Dak. Research Trials. With a 0-9 ranking scale (0=All plants upright, very easy to harvest; and 9=All plants flat, very difficult to harvest), cultivar Treasure had a ranking scale of 2.5; cultivar Spider had a ranking of 0.7; and PP-1804 had a ranking scale of 0. Treasure is a common standard to include in ND Research Trials.

As to increased disease resistance, Table 1 comprises resistance data for PP-1804 which was more resistant to disease than CDC 0001 and CDC 007. Table 2 comprises resistance data for PP-1804, which was more resistant to disease than PP-0555 and PP-0667.

A field pea seed can be produced by the process of crossing a field pea plant parent CDC 0001 with a field pea plant CRP 0132 (a single Plant Purification from CDC 0001) according to a single plant selection procedure of plant breeding to produce the field pea seed and comprise at least one trait in Table 1, wherein the single plant selection procedure comprises backcrossing until the at least one trait in Table 1 is dominant.

As to the uniform pea shape (a commercial processing benefit and consumer desired benefit), Table 2 comprises descriptions of peas of PP-1804 as spherical, whereas peas of PP-0555 and PP-0667 are not. The characteristics of the pea cultivar of this disclosure that creates the rounder seed shape is twofold: 1) larger pea pods; and 2) pea pod droop angle. The pea cultivar of this disclosure was actively bred to comprise larger pea pods, which allows more space for the seeds to growth without forced contact with other seeds. Also, as the pea seeds (and pods) grow and as they dry preharvest, the pods of the seed cultivar of this disclosure do not drop (or droop) toward the ground (and thus against the plant stem) as most pea plants do. This also allows the seeds to grow without shape effecting hindrances.

Embodiments of the current disclosure include all means of breeding to create pea cultivar PP-1804 and any progeny of PP-1804. Choice of breeding or selection methods depends on the mode of plant reproduction, the heritability of the trait(s) being improved, and the type of cultivar used commercially (e.g., $F_1$ hybrid cultivar, pure line cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

The breeders of the cultivar of this disclosure advanced promising breeding lines with thorough testing and comparison to appropriate standards in environments representative of the commercial target area(s). In this case, the best lines were candidates for a new commercial cultivar; those still deficient in a few traits were used as parents to produce the new populations for further selection.

These processes, which lead to the final step of marketing and distribution, may take from 2 to 12 years from the time the first cross is made. Therefore, development of new cultivars is a time-consuming process that requires precise forward planning, efficient use of resources, and a minimum of changes in direction. As well as the skill, creativity, and insight of the breeder.

A difficult task was the identification of individuals that were genetically superior, because for most traits the true genotypic value was masked by other confounding plant traits or environmental factors. The breeders of the current cultivar used a method of identifying a superior plant through observation of its performance relative to other experimental plants and to a widely grown standard cultivar (e.g., Treasure and Spicer).

The goal of field pea plant breeding is to develop new, unique and superior field pea cultivars and hybrids. The breeder of the current disclosure initially selected and crossed two parental lines, followed by repeated selfing and selection, producing many new genetic combinations. The breeder of the current disclosure could theoretically generate billions of different genetic combinations via crossing, selfing and mutations. The breeder had no direct control at the cellular level.

Each year, the plant breeder of the current cultivar disclosure selected the germplasm to advance to the next generation. This germplasm was grown under unique and different geographical, climatic and soil conditions, and further selections are then made, during and at the end of the growing season. The cultivars which were developed had some unpredictability. This unpredictability was because the breeder's selection occurred in unique environments, with no control at the DNA level (using conventional breeding procedures), and with millions of different possible genetic combinations being generated.

An embodiment of the current disclosure comprises the development of the new field pea cultivar of this disclosure by the development and selection of field pea varieties, the crossing of these varieties, and the selection of superior hybrid crosses. The hybrid pea is produced by crosses between selected fertile parents or by using male sterility systems. These hybrids are selected for certain single gene traits such as pod color, flower color, pubescence color, plant physical characteristics, seed content, or disease resistance which indicate that the pea is truly a hybrid.

An embodiment of the current disclosure comprises pedigree breeding and recurrent selection breeding methods that could be used to develop cultivars from breeding populations. Breeding programs would combine desirable traits from two or more cultivars or various broad-based sources into breeding pools from which cultivars would be developed by selfing and selection of desired phenotypes.

Pedigree breeding is used commonly for the improvement of self-pollinating crops. Two parents which possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars. An embodiment of the current disclosure comprises the use of mass and recurrent selections to find and/or create the cultivar of this disclosure (i.e., PP-1804 and its progeny), Mass and recurrent selections could be used to improve populations of either self- or cross-pollinating crops. A genetically variable population of heterozygous individuals could either be identified or created by intercrossing several different parents. The best plants would be selected based on individual superiority, outstanding progeny, or excellent combining ability. The selected plants would be intercrossed to produce a new population in which further cycles of selection are continued.

An embodiment of the current disclosure comprises the use of backcross breeding to find and/or create the cultivar of this disclosure (i.e., PP-1804 and its progeny), Backcross breeding could be used to transfer genes for a simply inherited, highly heritable trait into a desirable homozygous cultivar or inbred line which would be the recurrent parent. The source of the trait to be transferred would be called the donor parent. The resulting plant can comprise the attributes of the recurrent parent (e.g., cultivar) and the desirable trait transferred from the donor parent. After the initial cross, individuals possessing the phenotype of the donor parent would be selected and repeatedly crossed (backcrossed) to the recurrent parent. The resulting plant can comprise the attributes of the recurrent parent (e.g., cultivar) and the desirable trait transferred from the donor parent.

An embodiment of the current disclosure comprises the use of single-seed descent procedure to find and/or create the cultivar of this disclosure (i.e., PP-1804 and its progeny), The single-seed descent procedure in the strict sense could refer to planting a segregating population, harvesting a sample of one seed per plant, and using the one-seed sample to plant the next generation. When the population had been advanced from the $F_2$ to the desired level of inbreeding, the plants from which lines were derived would each trace to different $F_2$ individuals. The number of plants in a population would decline each generation due to failure of some seeds to germinate or some plants to produce at least one seed. As a result, not all of the $F_2$ plants originally sampled in the population would be represented by a progeny when generation advance was completed.

An embodiment of the current disclosure comprises the use of mutation breeding techniques to find and/or create the cultivar of this disclosure (i.e., PP-1804 and its progeny), Mutation breeding could be another method of introducing new traits into field pea varieties to create the cultivar of this disclosure. Mutations that occur spontaneously or are artificially induced could be useful sources of variability for a plant breeder. The goal of artificial mutagenesis would be to increase the rate of mutation for a desired characteristic. For example, breeder would plant a selected pea cultivar under normally adversarial conditions for that pea cultivar (such as high temperatures or sandy soil). The breeder would then spend time, energy, and creativity to gain the result of any natural mutation within the pea to create plants and peas with desirable traits useful for planting peas under those conditions. Once a desired trait was observed through this process, the desired trait would then be incorporated into existing germplasm by traditional breeding techniques. Mutation rates could be increased by many different means comprising temperature, long-term seed storage, and tissue culture conditions, as well as radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethylene amines, sulfates, sulfonates, sulfones, or lactones), azide, hydroxylamine, nitrous acid or acridness. Details of mutation breeding can be found in "Principles of Cultivar Development" by Fehr, Macmillan Publishing Company, 1993.

An embodiment of the current disclosure comprises the use of double haploids to find and/or create the cultivar of this disclosure (i.e., PP-1804 and its progeny). The production of double haploids could also be used for the development of homozygous varieties in a breeding program. Double haploids would be produced by the doubling of a set of chromosomes from a heterozygous plant so as to produce a completely homozygous individual.

Proper testing during breeding was used to detect any major faults and to establish the level of superiority or improvement over current cultivars. In addition to showing superior performance, the breeders of the current disclosure found a demand for the new cultivar that was compatible with industry standards and/or created a new market. The introduction of the new cultivar will incur additional costs to the seed (i.e., pea) producer, the grower, processor and consumer; for special advertising and marketing, altered seed and commercial production practices, and new product utilization. The testing preceding release of the new cultivar took into consideration research and development costs as well as technical superiority of the final new cultivar of the current disclosure. As it is a seed-propagated cultivar, the new cultivar had to be feasible to produce seed easily and economically.

Based on knowledge of soil and growing conditions, as well as knowledge of cultivar characteristics potentially available in breeding stock, along with the time and patience for repeated selfing and selection (with or without mutation breeding processes), the breeders of the current disclosure were able to develop a pea cultivar (i.e., PP-1804) with high protein content, uniform pea shape, increased tolerance to heat stress (including reduced shattering), and increased resistance to plant diseases.

An embodiment of the current disclosure comprises single or multiple gene converted plants of field pea cultivar PP-1804. The transferred gene(s) may be a dominant or recessive allele. The transferred gene(s) can confer such traits as high pea protein content, increased heat resistance, increased disease resistance, and uniform pea shape. The gene may be a naturally occurring field pea gene or a transgene introduced through genetic engineering techniques.

An embodiment of the current disclosure comprises regenerable cells for use in tissue culture of field pea plant PP-1804. The tissue culture can have a capability of regenerating plants comprising the physiological and morphological characteristic of the foregoing field pea plant, and of regenerating plants comprising substantially the same genotype as the foregoing field pea plant. The regenerable cells in such tissue cultures can be embryos, protoplasts, meristematic cells, callus, pollen, leaves, anthers, roots, root tips, flowers, seeds, pods or stems. Still further, the present disclosure provides field pea plants regenerated from the tissue cultures of this disclosure.

An embodiment of the current disclosure comprises methods for producing a field pea plant containing in its genetic material one or more transgenes of the cultivar of the current disclosure and to the transgenic field pea plants and plant parts produced by those methods. This disclosure also relates to field pea cultivars or breeding cultivars and plant parts derived from field pea cultivar PP 1804, to methods for producing other field pea cultivars, lines or plant parts derived from field pea cultivar PP-1804 and to the field pea plants, varieties, and their parts derived from use of those methods, comprising traditional breeding and genetic engineering. The disclosure further relates to hybrid field pea seeds, plants and plant parts produced by crossing field pea cultivar PP 1804 with another field pea cultivar.

Embodiments of this disclosure are also directed to methods for producing a field pea plant by crossing a first parent field pea plant with a second parent field pea plant, wherein the first or second field pea plant is the field pea plant for the field pea cultivar PP-1804. Further, both first and second parent field pea plants may be from field pea cultivar PP-1804. Therefore, any methods using field pea cultivar PP-1804 are part of this disclosure: selfing, backcrosses, hybrid breeding, and crosses to populations. Any plants produced using field pea cultivar PP-1804 as at least one parent are within the scope of this disclosure. This disclosure is also directed to methods of using field pea cultivar PP-1804 to reproduce morphological and/or physical characteristics of PP-1804 in other pea plants include but are not limited to use of expression vectors introduced into plant tissues using a direct gene transfer method such as microprojectile-mediated delivery, DNA injection, electroporation and the like. Expression vectors are introduced into plant tissues by using either microprojectile-mediated delivery with a biolistic device, of by using *Agrobacterium*-mediated transformation. Transformant plants obtained in the protoplasm of the disclosure are intended to be within the scope of this disclosure.

An embodiment of the current disclosure comprises a method of introducing a desired trait into field pea cultivar PP-1804 or its progeny. The method can comprise the steps of: (a) crossing a PP-1804 plant, representative seed having been deposited under ATCC Accession No. PTA-124820, with a plant of another field pea cultivar that comprises a desired trait to produce progeny plants wherein the desired trait is selected from the group consisting of male sterility, herbicide resistance, insect resistance, modified fatty acid metabolism, increased protein content, modified carbohydrate metabolism, or decreased phytate content, and resistance to bacterial disease, fungal disease or viral disease, increased shatter resistance, or combinations thereof; (b) selecting one or more progeny plants that comprise the desired trait to produce selected progeny plants; (c) crossing the selected progeny plants with the PP-1804 plants to produce backcross progeny plants; (d) selecting for backcross progeny plants that comprise the desired trait and physiological and morphological characteristics of field pea cultivar PP-1804 listed in Table 1 to produce selected backcross progeny plants; and (e) repeating steps (c) and (d) three or more times in succession to produce selected fourth or higher backcross progeny plants that comprise the desired trait and all of the physiological and morphological characteristics of field pea cultivar PP-1804 listed in Table 1.

Another embodiment of the method for producing an F1 hybrid field pea seed can comprise crossing the plant with a different field pea plant and harvesting at least one resultant F1 hybrid field pea seed.

An embodiment of the process of producing a field pea plant can comprise producing a field pea plant comprising increased disease resistance, increased shatter resistance, low Harvest Ease score or combination thereof from a pea seed, wherein the method comprises crossing field pea plant CDC 0001 with another pea cultivar according to single plant selection procedure of plant breeding and growing crossed seeds in dry environments.

Another embodiment of the method of producing a field pea plant with disease resistance, heat resistance, high protein content, or combinations thereof of the field pea plant can comprise transforming the field pea plant with a transgene that confers disease resistance, heat resistance, high protein content, or combinations thereof.

An embodiment of the process of producing a field pea plant can comprise producing a field pea plant comprising increased disease resistance, increased heat resistance, low Harvest Ease score or combinations thereof of pea seed, wherein the field pea plant is genetically engineered.

Another embodiment of the present disclosure can comprise a field pea plant, or a part thereof, can comprise a plant or plant part, that is resistant to a disease selected from the group consisting of Root Rot, *Mycosphaerella* Blight, Azchoch Root Rot, Powdery Mildew, and combinations thereof.

Another embodiment of the present disclosure can comprise a field pea plant comprising a Harvest Ease score of 0 to 2.5 on a 0-9 score scale.

Another embodiment of the present disclosure can comprise a field pea plant comprising a high heat resistance exhibited by increased shatter resistance, Harvest Ease score of less than 2.5, yield greater than 40 bushels/acre, or combinations thereof.

Another embodiment of the present disclosure can comprise a tissue culture of regenerable cells produced from the field pea plant, wherein said cells of the tissue culture are produced from a plant part selected from the group consisting of leaf, pollen, embryo, cotyledon, hypocotyl, meristematic cell, root, root tip, pistil, anther, flower, stem and pod.

An embodiment of the current disclosure comprises the use of molecular biological techniques in the finding and/or creation of the pea cultivar of this disclosure (PP-1804) and any progeny of that pea cultivar.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last twenty years several methods for producing transgenic plants have been developed and the present disclosure, in particular embodiments, also relates to transformed versions of the claimed cultivar or line.

Plant transformation involves the construction of an expression vector which will function in plant cells. Such a vector comprises DNA comprising a gene under control of, or operatively linked to, a regulatory element (for example, a promoter). The expression vector(s) may be in the form of a plastid and can be used alone or in combination with other plasmids to provided transformed field pea plants using transformation methods to incorporate transgenes into the genetic material of the field pea plants(s).

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" comprises reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids or sclerenchyma.

An inducible promoter is operably linked to a gene for expression in field pea. Optionally, the inducible promoter is operably linked to a nucleotide sequence encoding a signal sequence which is operably linked to a gene for expression in field peas. An inducible promoter can be used in the instant disclosure.

A constitutive promoter is operably linked to a gene for expression in field pea or the constitutive promoter is operably linked to a nucleotide sequence encoding a signal sequence with is operably linked to a gene for expression in field pea. Many different constructive promoters can be utilized in the instant disclosure.

A tissue-specific promoter is operably linked to a gene for expression in field pea. Optionally, the tissue-specific promoter is operably linked to a nucleotide sequence encoding a signal sequence which is operably linked to a gene for expression in field pea. Plants transformed with a gene of interest operably linked to a tissue-specific promoter product the protein product of the transgene exclusively, or preferentially, in a specific tissue. Any tissue-specific or tissue-preferred promoter can be utilized in the instant disclosure.

With transgenic plants according to the present disclosure, a foreign protein can be produced in commercial quantities. Thus, techniques for the selection and propagation of transformed plants, which are well understood in the art, yield a plurality of transgenic plants which are harvested in conventional manner and a foreign protein then can be extracted from a tissue of interest or from total biomass. Protein extraction from plant biomass can be accomplished by known methods.

According to an embodiment of the current disclosure, the transgenic plant provided for commercial production of foreign protein is a field pea plant. In another embodiment, the biomass of interest is seed (i.e., pea). For the relatively small number of transgenic plants that show higher levels of expression, a genetic map can be generated, primarily via conventional RFLP, PCR and SR analysis, which identified the approximate chromosomal location of the integrated DNA molecule. For exemplary methodologies in this regard, see Glick and Thompson, Methods in Plant Molecular Biology and Biotechnology, (CRC Press, Boca Raton) 269: 284 (1993). Map information concerning chromosomal locations is useful for proprietary protection of a subject transgenic plant. If unauthorized propagation is undertaken and crosses made with other germplasm, the map of the integration region can be compared to similar maps for suspect plants, to determine if the latter comprise a common parentage with the subject plant. Map comparisons would involve hybridizations, RFLP, PCR, SSR and sequencing, all of which are conventional techniques.

Likewise, by means of the present disclosure, agronomic genes can be expressed in transformed plants. An embodiment of the current disclosure comprises use of genetic engineering techniques to genetically engineer pea plants to express various phenotypes of agronomicnterest, such as increased pea protein content, increased heat resistance, and/or increased disease resistance. Exemplary genes implicated in this regard comprise those categorized as genes that confer resistance to pests or disease, genes that confer resistance to an herbicide, genes that confer increased heat resistance, and genes that confer or contribute to a value added trait (e.g., pea protein content and pea physical shape).

As to genes that confer resistance to pests or disease: plant defenses are often activated by specific interaction between the product of a disease resistance gene (R) in the plant and the product of a corresponding avirulence (Ar) gene in the pathogen. A plant cultivar can be transformed with one or more cloned resistance genes to engineer plants that are resistant to specific pathogen strains. Engineered plants that contain these genes are intended to be within the scope of this disclosure.

As to genes that confer resistance to ah herbicide, a herbicide that inhibits the growing point or meristem, such as an imidazlinone or a sulfonylurea, or a herbicide that inhibits photosynthesis. A plant cultivar can be transformed with one of more of cloned resistance genes to engineered plants that are resistant to specific herbicides. Engineered plants that contain these genes are intended to be within the scope of this disclosure.

As to genes that confer or contribute to a value-added trait, such as modified carbohydrate composition, a transformation of a plant cultivar can comprise an effected and increased protein content. Engineered plants that contain these genes that code (or confer) a value-added trait are intended to be within the scope of this disclosure.

Numerous methods for plant transformation have been developed, including biological and physical plant transformation protocols. The use of any of these transformations to find and/or create the pea cultivar of the current disclosure (pp-1804 and its progeny) are intended to be within the scope of this disclosure. Such methods for field pea transformation can include, but are not limited to: 1. *Agrobacterium*-mediated transformation and 2. Direct gene transfer.

The foregoing methods for transformation would typically be used for producing a transgenic cultivar. The transgenic cultivar could then be crossed with another (non-transformed or transformed) cultivar, in order to produce a new transgenic cultivar. Alternatively, a genetic trait which has been engineered into a particular field pea line using the foregoing transformation techniques could be moved into any of the line using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar or cultivars which do not contain that gene. As used herein, "crossing" can refer to a simple X by Y cross, or the process of backcrossing depending on the context.

When the term field pea plant or pea plant is used in the context of the present disclosure, it also comprises any single gene conversions of that cultivar. The term single gene converted plant as use herein refers to those field pea plants which are developed by a plant breeding technique called backcrossing wherein essentially all of the desired morphological and physiological characteristics of a cultivar are recovered in addition to the single gene transferred into the cultivar via the backcrossing technique. Backcrossing methods can be used with the present disclosure to improve or introduce a characteristic into the cultivar. The term backcrossing as used herein refers to the repeated crossing of a hybrid progeny back to the recurrent parent, i.e., crossing back 1, 2, 3, 4, 5, 6, 7, 8, 9, or more times to the recurrent parent. The parental field pea plant which contributes the gene for the desired characteristic is termed the nonrecurrent or donor parent. This terminology refers to the fact that the nonrecurrent parent is used one time in the backcross protocol and therefore does not recur. The parental field pea plant to which the gene or genes from the nonrecurrent parent are transferred is known as the recurrent parent as it is used from several rounds in the backcrossing protocol. In a typical backcross protocol, the original cultivar of interest (recurrent parent) is crossed to a second cultivar (nonrecurrent parent) that carries the single gene of interest to be transferred. The resulting progeny from this cross are then crossed again to the recurrent parent and the process is repeated until a field pea plant is obtained wherein essentially all of the desired morphological and physiological characteristics of the recurrent parent are recovered in the converted plant, in addition to the single transferred gene from the nonrecurrent parent as determined at the 5% significance level when grown in the same environmental conditions.

The selection of a suitable recurrent parent is an important step for a successful backcrossing procedure. The goal of a backcross protocol is to alter or substitute a single trait or characteristic in the original cultivar. To accomplish this, a single gene of the recurrent cultivar is modified or substituted with the desired gene from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic; examples of these traits can include by are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus.

Further reproduction of the cultivar of the current disclosure can occur by tissue culture and regeneration, which is within the scope of this disclosure Tissue culture of various plant tissues and regeneration of plants therefrom is well known and widely published. Thus, another aspect of this disclosure is to provide cells which, upon growth and differentiation, produce field pea plants comprising the physiological and morphological characteristic of field pea cultivar PP-1804.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants.

An embodiment of this disclosure is directed to methods for producing the cultivar of the current disclosure (pp-1804 and its progeny) by crossing a first parent field pea plant with a second parent filed pea plant wherein the first or second parent field pea plant is a field pea plant of field pea cultivar PP-1804. Further, both first and second parent field pea plants can come from field pea cultivar PP-1804. Thus, any such methods using the field pea cultivar PP-1804 are part of this disclosure: selfing, backcrosses, hybrid production, crosses to populations, and the like. All plants produced using field pea cultivar PP-1804 as at least one parent are within the scope of this disclosure, comprising those developed from varieties derived from field pea cultivar PP-1804. This field pea cultivar could be used in crosses with other, different, field pea plants to produce first generation ($F_1$) field pea hybrid seeds and plants with superior characteristics. The cultivar of this disclosure can also be used for transformation where exogenous genes are introduced and expressed by the cultivar of the disclosure. Genetic variants created either through traditional breeding methods using field pea cultivar PP-1804 or through transformation of field pea cultivar PP-1804 by any number of protocols known to those of skill in the art are intended to be within the scope of this disclosure. An embodiment of the current disclosure comprises use of the following breeding methods that uses the pea cultivar PP 1804 in the development of further field pea plant cultivars, which would be embodiments of the current disclosure. One such embodiment would be a method for developing a field pea plant breeding program comprising: obtaining the field pea pant, or a part thereof, of field pea cultivar PP-1804 utilizing said plant or plant part as a source of breeding material, and selecting a field pea cultivar PP-1804 progeny plant with molecular markers in common with field pea cultivar PP-1804 and/or with morphological and/or physiological characteristics selected from the characteristics listed in Table 1. Breeding steps that could be used in the field pea plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method that is an embodiment of the current disclosure involves producing a population of field pea cultivar PP-1804 progeny field pea plants, comprising crossing filed pea cultivar PP-1804 with another field pea plant, thereby producing a population of field pea plants, which on average, derive 50% of their alleles from field pea cultivar PP-1804. A plant of this population may be selected and repeatedly selfed or sibbed with a field pea cultivar resulting from these successive filial generations. One embodiment of this disclosure is the field pea cultivar produced by this method and that has obtained at least 50% of its alleles from field pea cultivar PP-1804.

One of ordinary skill in the art of plant breeding would know how to evaluate the traits of two plant varieties to determine if there is no significant difference between the two traits expressed by those varieties. Thus the current disclosure comprises field pea cultivar PP-1804 progeny field pea plants comprising a combination of at least two PP-1804 traits selected from the group consisting of those listed in Table 1 or the PP-1804 in combination with other desirable traits so that said progeny field pea plant is not significantly different for said traits than field pea cultivar PP-1804 as determined at the 5% significance level when grown in the same environmental conditions. Using techniques described herein, molecular markers may be used to identify said progeny plant as a PP-1804 progeny plant. Mean trait values may be used to determine whether trait differences are significant, and preferably the traits are measured in plants grown under the same environmental conditions. Once such a cultivar is developed its value is substantial since it is important to advance the germplasm base as a whole in order to maintain or improve traits such as yield, disease resistance, pest resistance, and plant performance in extreme environmental conditions.

Progeny of field pea cultivar PP-1804 may also be characterized through their filial relationship with field pea cultivar PP-1804, as for example, being with a certain number of breeding crosses of field pea cultivar PP-1804. A breeding cross is a cross made to introduce new genetics into the progeny, and is distinguished from a cross, such as a self or a sib cross, made to select among existing genetic alleles. The lower the number of beading crosses in the pedigree, the closer the relationship between field pea cultivar PP-1804 and its progeny. For example, progeny produced by the methods described herein may be within 1, 2, 3, 4, or 5 breeding crosses of field pea cultivar PP-1804.

As used herein, the term plant comprises plant cells, plant protoplasts, plant cell tissue cultures from which field pea plants can be regenerated, plant calli, plant clumps and plant cells that are intact in plants or parts of plants, such as embryos, pollen, ovules, flowers pods, leaves, roots, root tips, anthers, and the like.

In and embodiment of this disclosure, the seed of field pea cultivar PP-1804, the plant produced from the seed, the hybrid field pea plant produced from the crossing of the cultivar with any other field pea plant, hybrid seed, and various parts of the hybrid field pea plant can be utilized as a commercial commodity, or to make a commercial commodity, as is or in the production of a human food, livestock food, or new material in industry. Such human food, livestock food, or new material could be comprised in whole or in part of matter from peas of the current disclosure (pp-1804 and its progeny). The matter could be from all parts of the peas or from only selected parts of the peas, such as protein, fiber, carbohydrate, ash, lipid or any combination of thereof.

Further embodiments of the current disclosure include:

A. A field pea plant, or a part thereof, produced by growing the seed of field pea cultivar PP-1804, wherein a representative sample of seed of said cultivar was deposited under ATCC Accession No. PTA-124820, further comprising at least one transgene.

B. The field pea plant of A, wherein the at least one transgene confers upon the field pea plant resistance to bacterial disease, viral disease, or fungal disease, or combination thereof.

C. The field pea plant of A, wherein the at least one transgene confers upon the field pea plant drought tolerance or salt tolerance.

D. The field pea plant of A, wherein the at least one transgene confers upon the field pea plant shattering resistance.

E. A method of producing field pea plant seed of pea cultivar PP-1804, comprising planting the seed of under conditions that result in the germination of the seed, growth of field pea plants and setting of progeny seed; and harvesting the progeny seed.

F. A method of producing a drought tolerant field pea plant, comprising: crossing a first field pea plant with at least one other field pea plant to produce progeny field pea plants, wherein the first field pea plant is the field pea plant of pp-1804; screening the progeny field pea plants to select a progeny field pea plant that is tolerant to drought conditions.

G. A method of producing a shatter resistant field pea plant, comprising: crossing a first field pea plant with at least one other field pea plant to produce progeny field pea plants, wherein the first field pea plant is the field pea plant PP-1804; screening the progeny field pea plants to select a progeny field pea plant that is resistant to shattering.

H. A method of producing a field pea plant with characteristics that will give it a Harvest Ease score of 0 to 1, comprising: crossing a first field pea plant with at least one other field pea plant to produce progeny field pea plants, wherein the first field pea plant is the field pea plant PP-1804; screening the progeny field pea plants to select a progeny field pea plant that has the characteristics to give it a Harvest Ease score of o to 1.

I. A process of producing a commodity plant product comprising: obtaining the field pea plant of PP-1804 or a part thereof; and producing the commodity plant product therefrom.

J. The process of I, wherein the commodity plant product is protein powder, protein concentrate, protein isolate, pea fiber, pea starch, pea meal, pea flour, pea hulls, or combinations thereof.

K. The process of J, wherein the commodity plant product is used in making food products, comprising beverages, sauces, bakery, snacks, meat analogs, aerated desserts and confectionary, non-dairy milks, and combinations thereof. The list of food products above is not exhaustive.

L. A food product comprising the commodity plant product of I.

M. A food product of I further comprising proteins, starches, fibers, flours, or combinations thereof from non-pea sources selected from the group consisting of beans, soybeans, chickpeas, sunflower seed, pumpkin, lentils, rice, oats, wheat, rye, tapioca, corn and combinations thereof.

The commodity plant product of I, wherein the commodity plant product is further modified by treatments selected from the group consisting of heating, milling, cooking, extruding, steaming, hydrolyzing, emulsifying, hydrogenating, acidifying, buffering, chemical modifying, and combinations thereof.

Deposit Information

A deposit of the proprietary field pea cultivar designated PP-1804 disclosed above and recited in the appended claims has been made with the American Type Culture Collection (ATCC), 10801 University Boulevard, Manassas, Va. 20110. The date of deposit was Jan. 25, 2018. The deposit of 2500 seeds was taken from the same deposit maintained by GTE, since prior to the filing date of this application. All restrictions upon the deposit have been removed, and the deposit is intended to meet all of the requirements of 37 CFR § 1.801-1.809. The ATCC accession number is PTA-124820. The deposit will be maintained in the depository for a period of 30 years, or 5 years after the last request, or for the effective life of the patent, whichever is longer, and will be replace as necessary during that period.

In sum, it is important to recognize that this disclosure has been written as a thorough teaching rather than as a narrow dictate or disclaimer. Reference throughout this specification to "one embodiment", "an embodiment", or "a specific embodiment" means that a particular feature, structure, or characteristic described in connection with the embodiment is included in at least one embodiment and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment may be combined in any suitable manner with one or more other embodiments. It is to be understood that other variations and modifications of the embodiments described and illustrated herein are possible in light of the teachings herein and are to be considered as part of the spirit and scope of the present subject matter.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise. Variation from amounts specified in this teaching can be "about" or "substantially," so as to accommodate tolerance for such as acceptable manufacturing tolerances.

The foregoing description of illustrated embodiments, including what is described in the Abstract and the Modes, and all disclosure and the implicated industrial applicability, are not intended to be exhaustive or to limit the subject matter to the precise forms disclosed herein. While specific embodiments of, and examples for, the subject matter are described herein for teaching-by-illustration purposes only, various equivalent modifications are possible within the spirit and scope of the present subject matter, as those skilled in the relevant art will recognize and appreciate. As indicated, these modifications may be made in light of the foregoing description of illustrated embodiments and are to be included, again, within the true spirit and scope of the subject matter disclosed herein.

Thus, although the foregoing disclosure has been described in some detail by way of illustration and example for purposes of clarity and understanding, it will be obvious that certain changes and modifications such as single gene modifications and mutations, somaclonal variants, variant individuals selected from large populations of the parts of the instant field pea cultivar and the like may be practiced within the scope of the invention, as limited only by the scope of claims.

We claim:

1. A seed of field pea cultivar PP-1804, wherein a representative sample of seed of said cultivar was deposited under ATCC Accession No. PTA-124820.

2. A field pea plant, or a part thereof, produced by growing the seed of claim 1.

3. A tissue culture of regenerable cells produced from the field pea plant of claim 2, wherein said cells of the tissue culture are produced from a plant part selected from the group consisting of leaf, pollen, embryo, cotyledon, hypocotyl, meristematic cell, root, root tip, pistil, anther, flower, stem and pod.

4. A field pea plant, or part thereof, produced by growing the seed of claim 1, wherein the plant comprises morphological and physiological characteristics of cultivar PP-1804.

5. A field pea plant, or part thereof, produced by growing the seed of claim 1, wherein the field pea plant comprises some disease resistance to Root Rot, *Mycosphaerella* Blight, Azchoch Root Rot, Powdery Mildew, and combinations thereof, and comprises a seed protein content of about 22% to about 30%.

6. A field pea plant, or part thereof, produced by growing the seed of claim 1, wherein the field pea plant comprises a high heat resistance exhibited by increased shatter resistance, Harvest Ease score of less than 2.5, yield greater than 40 bushels/acre, or combinations thereof.

7. A field pea plant, or part thereof, produced by growing the seed of claim 1, wherein the plant comprises a protein content of about 22% to about 30% and a yield of greater than 40 bushels/acre.

8. A method for producing an $F_1$ hybrid field pea seed, wherein the method comprises crossing the plant of claim 2 with a different field pea plant and harvesting at least one resultant F₁ hybrid field pea seed.

9. A hybrid field pea seed produced by the method of claim 8.

10. A hybrid field pea plant, or a part thereof, produced by growing said hybrid seed of claim 9.

11. A method of producing a field pea plant with disease resistance, heat resistance, high protein content, or combinations thereof of the field pea plant of claim 2, wherein the method comprises transforming the field pea plant of claim 2 with a transgene that confers disease resistance, heat resistance, high protein content, or combinations thereof.

12. The field pea plant, or a part thereof, of claim 11, wherein the plant or plant part is resistant to a disease selected from the group consisting of Root Rot, *Mycosphaerella* Blight, Azchoch Root Rot, Powdery Mildew, and combinations thereof.

13. The field pea plant of claim 11, wherein the plant comprises a Harvest Ease score of 0 to 2.5 on a 0-9 score scale.

14. A process of producing a field pea plant with increased disease resistance, increased heat resistance, low Harvest Ease score or combinations thereof of pea seed in claim 1, wherein the process comprises transgenic engineering.

15. A method of introducing a desired trait into field pea cultivar PP-1804 or its progeny, wherein the method comprises:
  (a) crossing a PP-1804 plant, representative seed having been deposited under ATCC Accession No. PTA-124820, with a plant of another field pea cultivar that comprises a desired trait to produce progeny plants wherein the desired trait is selected from the group consisting of male sterility, herbicide resistance, insect resistance, modified fatty acid metabolism, increased protein content, modified carbohydrate metabolism, or decreased phytate content, and resistance to bacterial disease, fungal disease or viral disease, increased shatter resistance, or combinations thereof;
  (b) selecting one or more progeny plants that comprise the desired trait to produce selected progeny plants;
  (c) crossing the selected progeny plants with the PP-1804 plants to produce backcross progeny plants;
  (d) selecting for backcross progeny plants that comprise the desired trait and physiological and morphological characteristics of field pea cultivar PP-1804 listed in Table 1 to produce selected backcross progeny plants; and
  (e) repeating steps (c) and (d) three or more times in succession to produce selected fourth or higher backcross progeny plants that comprise the desired trait and all of the physiological and morphological characteristics of field pea cultivar PP-1804 listed in Table 1.

16. A method of introducing a desired trait into field pea cultivar PP-1804, wherein the method involves transgenic engineering.

17. A plant produced by the method of claim 16, wherein the plant comprises a transgene that confers disease resistance, heat resistance, high protein content, or combinations thereof.

18. A process of producing a commodity plant product comprising: obtaining the field pea plant of claim 2 or a part thereof; and producing the commodity plant product therefrom, wherein the commodity plant product is protein powder, protein concentrate, protein isolate, pea fiber, pea starch, pea meal, pea flour, pea hulls, or combinations thereof.

19. The method of claim 18, further comprising making at least one food product selected from the group of beverages, sauces, bakery, snacks, meat analogs, aerated desserts and confectionary, non-dairy milks, or combinations thereof from the commodity plant product.

20. The method of claim 18, further comprising modifying the commodity plant product by at least one treatment selected from the group consisting of heating, milling, cooking, extruding, steaming, hydrolyzing, emulsifying, hydrogenating, acidifying, buffering, chemical modifying, or combinations thereof.

* * * * *